Oct. 21, 1952 G. L. JORDAN Plant Pat. 1,139
ROSE PLANT
Filed Oct. 12, 1951
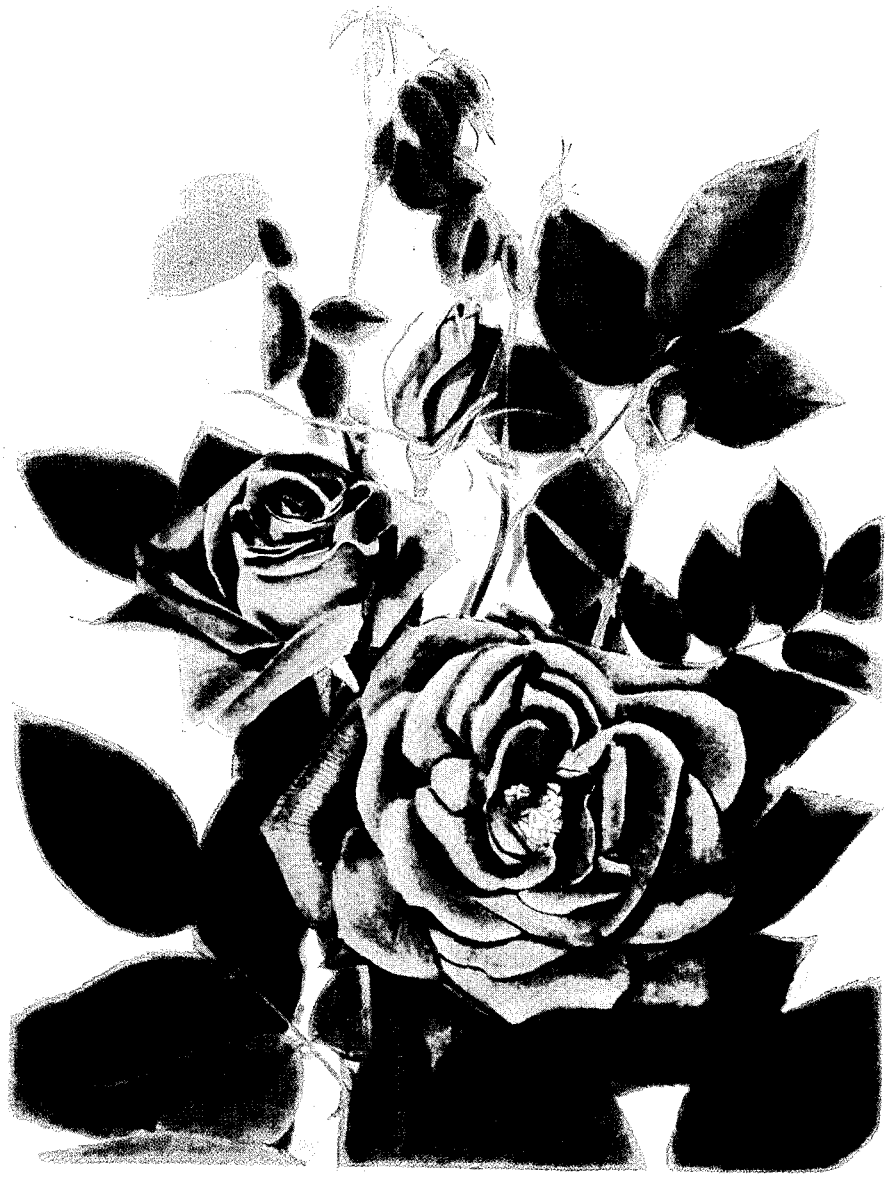
Inventor.
G. L. Jordan
By: Robert Cobb
Attorney.

Patented Oct. 21, 1952

Plant Pat. 1,139

UNITED STATES PATENT OFFICE 1,139

ROSE PLANT

Garret L. Jordan, Urbana, Ill., assignor to Jackson & Perkins Company, Newark, N. Y., a corporation of New York Application October 12, 1951, Serial No. 251,033

1 Claim. (Cl. 47—61)

The present invention relates to a new and distinct variety of rose plant of the hybrid tea class, originated by me by crossing the varieties "Crimson Glory" (Plant Patent No. 105) × "Poinsettia" (unpatented).

The primary object of the invention was to obtain a new variety of rose plant having substantially the growth and upright habits of "Poinsettia," but which bears flowers having substantially the color and fragrance of "Crimson Glory." This objective was fully achieved in the new variety, as evidenced by its upright growth and stiff neck, the great number of flowers produced when it is grown under greenhouse conditions, and by the Carmine general tonality and the graceful form of the blooms.

Asexual reproduction of the new variety by budding at Newark, New York, and at Pleasanton, California, shows that the foregoing characteristics come true to form and are established and transmitted through succeeding propagations.

The accompanying drawing shows specimens of the flowers and foliage of the new variety in different stages of development.

The following is a detailed description of the new variety, with color terminology in accordance with Ridgway's Color Standards and Nomenclature:

Parentage: Seedling.
*Seed parent.*—"Crimson Glory."
*Pollen parent.*—"Poinsettia."
Classification: Botanic and commercial—hybrid tea.

*Flower*

(Observations made at Newark, New York, in the greenhouse early in the morning in the month of December.)

Blooming habit: Recurrent—continuous.
Bud:
*Size.*—Large.
*Form.*—Ovoid. Is not affected by wet or hot weather.
*Color.*—When sepals first divide—Victoria Lake, Plate 1. When petals begin to unfurl—Oxblood Red, Plate 1. When half blown: inside of petals—Carmine, Plate 1, lightly overcast with Oxblood Red, Plate 1; reverse of petals—Pomegranate Purple, Plate 12.
*Sepals.*—Branched; "hood" above bud. Curl back when petals begin to unfurl. Color: inside—Light Lumiere Green, Plate 17; reverse—Biscay Green, Plate 17.
*Calyx.*—Shape—pear. Size—long. Aspect— smooth. Odor when rubbed—none. Color—Biscay Green, Plate 17.
*Peduncle.* — Length — medium. Aspect — smooth. Color — Oil Green, Plate 5. Strength—stiff; slender.
*Opening.*—Opens up well. Is not affected by adverse weather conditions.
Bloom:
*Size.*—Large. Average size when fully expanded—5 inches.
*Borne.*—Several together.
*Stems.*—Medium length; strong.
*Form.*—When first open—high center. Permanence—outer petals curl back.
*Petalage.*—Double (full but open center). Number of petals under normal conditions—30.
*Color.*—Center of flower—Carmine, Plate 1. Outer petals—Carmine, Plate 1, overcast lightly with Pomegranate Purple, Plate 12. Base of petals (aiglet)—Barium Yellow, Plate 16. Inside of petals—Carmine, Plate 1, overcast very lightly with Rose Red, Plate 12. Reverse of petals—Pomegranate Purple, Plate 12, lightly overcast with Tyrian Rose, Plate 12. General tonality from a distance—Carmine, Plate 1.
*Discoloration.*—General tonality at end of first day—Carmine, Plate 1. Second day—Carmine, Plate 1, overcast with Pomegranate Purple, Plate 12. Third day—Carmine, Plate 1, lightly overcast with Rose Red, Plate 12.
Petals:
*Texture.*—Thick. Is not affected by wet or hot weather.
*Appearance.*—Inside—velvety; outside— satiny.
*Form.*—Round.
*Arrangement.*—Irregular. Petaloids in center—few; small.
*Persistence.*—Drop off cleanly.
*Fragrance.* — Strong. Nature — "Old Rose perfume" (Centifolia).
*Lasting quality.*—On the plant and as cut flower—long.
Genital organs:
*Stamens, anthers.*—Medium size; many. Color—Chamois, Plate 30. Arrangement—regular around styles.
*Stamens, filaments (threads).* — Long. Color—Rose Doree, Plate 1.
*Pollen.*—Color—Massicot Yellow, Plate 16.
*Styles.*—Bunched; uneven length; short; thin.

*Stigmas.*—Color—Straw Yellow, Plate 16.
*Ovaries.*—All enclosed in calyx.
*Hips.*—None set or observed.

*Plant*

Form: Bush.
Growth: Vigorous; upright.
Foliage: 5 to 7 leaflets.
*Size.*—Large.
*Quantity.*—Normal abundance.
*Color.*—New foliage: upper side—Yellowish Oil Green, Plate 5, overcast with Oxblood Red, Plate 1; under side—Oxblood Red, Plate 1, overcast with Yellowish Oil Green, Plate 5. Old foliage: upper side—Elm Green, Plate 17; under side—Light Cress Green, Plate 31.
*Shape.*—Oval pointed.
*Texture.*—Upper side — leathery. Under side—smooth. Ribs and veins—ordinary.
*Edge.*—Serrated (saw toothed).
*Serration.*—Single; small.
*Leaf stem.*—Color—Light Cress Green, Plate 31. Under side—rough.
*Stipules.*—Medium length; smooth.

Wood:
*New Wood.*—Color—Hay's Russet, Plate 14. Bark—smooth.
*Old wood.*—Color—Cress Green, Plate 31. Bark—smooth.
Thorns:
*Thorns.*—Quantity — on main stalks from base and on laterals from stalk—ordinary. Form — narrow base; medium length; hooked downward. Color when young—Rose Doree, Plate 1. Position—irregular.
*Prickles.*—Quantity—on main stalks and on laterals—none.
*Short needles.*—Quantity—on main stalks and on laterals—none.

I claim:

A new and distinct variety of rose plant of the hybrid tea class, substantially as herein shown and described, characterized as to novelty by its upright habit of growth, its stiff neck and the great number of flowers produced thereby when grown under greenhouse conditions, and by the graceful form and Carmine general tonality of its blooms.

GARRET L. JORDAN.

No references cited.